United States Patent [19]

Schoenleben

[11] Patent Number: 4,897,480
[45] Date of Patent: Jan. 30, 1990

[54] PREPARATION OF N,N'-DIALKYL SUBSTITUTED CYCLIC UREA DERIVATIVES

[75] Inventor: Willibald Schoenleben, Heidelberg, Fed. Rep. of Germany

[73] Assignee: Basf Aktiengesellschaft, Ludwigshafen, Fed. Rep. of Germany

[21] Appl. No.: 284,245

[22] Filed: Dec. 14, 1988

[30] Foreign Application Priority Data

Dec. 24, 1987 [DE] Fed. Rep. of Germany ....... 3744120

[51] Int. Cl.$^4$ .................. C07D 239/10; C07D 233/32
[52] U.S. Cl. ...................................... 544/315; 548/317
[58] Field of Search ......................... 548/317; 544/315

[56] References Cited

U.S. PATENT DOCUMENTS 2,497,308  2/1950  Larson ................................ 548/317
4,642,351  2/1987  Woo et al. ........................... 548/317

FOREIGN PATENT DOCUMENTS 0280781  9/1988  European Pat. Off. .

OTHER PUBLICATIONS

P. Shenoy, et al., *Am. Dyestuff Rep.*, 57, 1968, 352–360.
J. Mulvaney, et al., *Ind. Eng. Chem.* 40, 1948, 393–397.
R. Nomura et al., *Ind. Eng. Chem. Res.*, 26, 1987, 1056–1059.
*Chem. Abstracts* 98, 126094a, (1983), (Jpn. Kokai Tokyo Koho JP 57, 175, 170, 10/28/83).

*Primary Examiner*—Richard A. Schwartz
*Attorney, Agent, or Firm*—Keil & Weinkauf

[57] ABSTRACT

N,N'-dialkyl-substituted cyclic urea derivatives of the general formula I

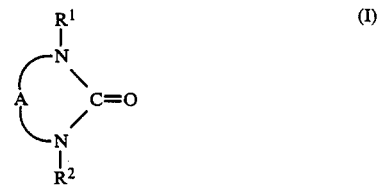

where $R^1$ and $R^2$ are each alkyl of 1 to 8 carbon atoms and A is $CR^3R^4$-$CR^5R^6$- or $CR^3R^4$-$CR^5R^6$-$CR^7R^8$, where $R^3$ to $R^8$ are each hydrogen or alkyl of 1 to 17 carbon atoms, are prepared by reacting a diamine of the formula II

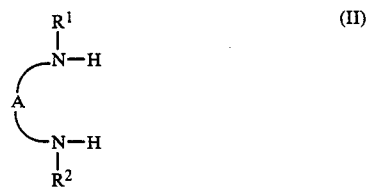

with carbon dioxide, by a method in which the reaction is carried out in the gas phase in the presence of an oxide of an element of main group three or four or subgroup two to six of the Periodic Table, or a mixture of these, or in the presence of an aluminum silicate or magnesium silicate.

1,3,4-trimethyl-2-imidazolidinone is used as a polar solvent at low temperatures.

7 Claims, No Drawings

PREPARATION OF N,N'-DIALKYL SUBSTITUTED CYCLIC UREA DERIVATIVES

The present invention relates to a process for the preparation of N,N'-dialkyl-substituted cyclic urea derivatives of the general formula I

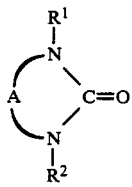

(I)

where $R^1$ and $R^2$ are each alkyl of 1 to 8 carbon atoms and A is $CR^3R^4$-$CR^5R^6$ or $CR^3R^4$-$CR^5R^6$-$CR^7R^8$, where $R^3$ to $R^8$ are each hydrogen or alkyl of 1 to 17 carbon atoms, by reacting a diamine of the general formula II

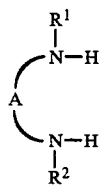

(II)

with carbon dioxide in the gas phase in the presence of an oxide catalyst.

These compounds may also be regarded as cyclic urea derivatives.

The present invention furthermore relates to the compound 1,3,4-trimethyl-2-imidazolidinone.

The N,N'-dialkyl-substituted cyclic urea derivatives, being polar, aprotic solvents, are of industrial interest. They are used for dissolving drugs, high molecular weight substances, such as polyamides, PVC, polystyrene, polyurethane, etc., and inorganic compounds, and serve as media in chemical reactions.

Although there are some known methods for the preparation of N,N'-dialkyl-substituted urea derivatives, these methods require starting materials which are expensive or difficult to handle, or give only moderate yields. An overview of the preparation method is given by Shenoy and Pearce (Am. Dyestuff Rep. 57 (1968), 352). For example, diamines of the N,N'-dimethylethylenediamine type can be cyclized with urea, diethyl carbonate or phosgene to give a 5-membered ring.

Even more advantageous than urea would be the use of carbon dioxide as a cheap cyclization agent which is easy to handle. Although it is known that ethylenediamine and $CO_2$ can be subjected to a thermal reaction at 200-300° C. to give ethyleneurea (e.g. U.S. Pat. No. 2,497,308 and Mulvaney and Evans, Ind. Eng. Chem. 40 (1948), 393), the purely thermal method is unsuccessful in the case of the N-substituted diamines. Normura et al. (Ind. Eng. Chem. Res. 1987, 1056-1059) therefore catalyze the reaction with triphenylstibine oxide, $Ph_3SbO$, in the presence of a zeolite, but obtain 1-methyl-2-imidazolidinone in a yield of only 85%.

According to Japanese Preliminary Published Application 57/175 170 (Chem. Abstracts 98, 126094a), 1,3-dimethyl-2-imidazolidinone is prepared by heating N,N'-dimethylethylenediamine and $CO_2$ in the presence of methylamine to 210° C. in an autoclave. However, the yield is only 85% of theory.

It is an object of the present invention to provide a process which makes it possible to obtain N,N'-dialkyl-substituted cyclic urea derivatives in good yields and in an economical manner by reacting an N,N'-dialkyldiamine II with carbon dioxide. It is a further object of the present invention to provide 1,3-dialkyl-2-imidazolidinones, which, being polar solvents, can be used for high molecular weight compounds at low temperatures.

We have found that this object is achieved and that N,N'-dialkyl-substituted cyclic urea derivatives of the formula I

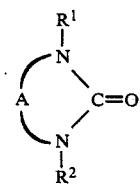

(I)

where $R^1$ and $R^2$ are each alkyl of 1 to 8 carbon atoms and A is $CR^3R^4$-4 $CR^5R^6$ or $CR^3R^4$-$CR^5R^6CR^7R^8$, where $R^3$ to $R^8$ are each hydrogen or alkyl of 1 to 17 carbon atoms, can advantageously be prepared by reacting a diamine of the general formula II

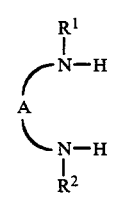

(II)

with carbon dioxide in the gas phase by a method in which the reaction is carried out in the presence of an oxide of an element of main group three or four or subgroup two to six of the Periodic Table, or a mixture of these, or in the presence of an aluminum silicate or magnesium silicate.

Examples of catalysts which are suitable for the novel process are acidic, oxidic heterogeneous catalysts and in particular oxidic compounds which have both acidic and basic properties, for example aluminas, i particular $\gamma$-$Al_2O_3$, aluminum silicates or zinc oxide. Instead of aluminum silicates, magnesium silicates or mixtures of aluminum silicates and magnesium silicates are also suitable. Instead of using the oxidic compounds directly, it is also possible to employ compounds which are converted into the oxides under the reaction conditions, for example aluminum hydroxides or aluminum oxide hydroxides.

The following oxidic catalysts may be mentioned by way of example: silica in the form of silica gel, kieselguhr or quartz, aluminas, boron oxide, zinc oxide, titanium dioxide, zirconium dioxide, vanadium oxides, niobium oxides, chromium oxides, molybdenum oxides, tungsten oxides and pumice or mixtures of these oxides, such as $SiO_2 \cdot Al_2O_3$, $B_2O_3 \cdot Al_2O_3$, $Cr_2O_3 \cdot Al_2O_3$, $MoO_3 \cdot Al_2O_3$ or $ZrO_2 \cdot SiO_2$.

Other suitable catalysts are zeolite catalysts. Zeolites are crystalline aluminosilicates which have a highly ordered structure with a rigid three-dimensional network of $SiO_4$ and $AlO_4$ tetrahedra which are bonded by common oxygen atoms. The ratio of the Si and Al atoms to oxygen is 1:2 (see Ullmanns Encyclopädie d. techn. Chemie, 4th Edition, Volume 24, page 575, 1983). The electrovalency of the aluminum-containing tetrahedra is balanced by the inclusion of cations in the crystal, for example an alkali metal ion or a hydrogen ion. Cation exchange is also possible.

In the zeolites, it is also possible for other elements, such as B, Ga, Fe, Cr, V, As, Sb, Bi or Be, or a mixture of these, to be incorporated in the framework instead of aluminum, or for the silicon to be replaced by a tetravalent element, such as Ge, Ti, Zr or Hf.

Depending on their structure, zeolites are divided into various groups (cf. Ullmanns Encyclopädie d. techn. Chemie, 4th Edition, Volume 24, page 575, 1983). For example, the zeolite structure is formed by chains of tetrahedra in the mordenite group and by sheets of tetrahedra in the chabasite group, while in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made between zeolites of type A, L, X and Y.

Examples of catalysts which are suitable for the novel process are zeolites from the mordenite group or fine-pore zeolites of the erionite or chabasite type or zeolites of the faujasite type, eg. Y, X or L zeolites, as well as pentasil zeolites, which have, as a common basic building block, a 5-membered ring consisting of $SiO_4$ tetrahedra. They possess a high $SiO_2/Al_2O_3$ ratio of about 10 to 40,000 and pore sizes which are between those of the zeolites of type A and those of type X or Y. Their preparation is described in, for example, German Laid-Open Applications DOS 3,513,725 or DOS 3,506,632.

The catalysts which can be used according to the invention can be modified by treatment with acids, for example phosphoric acid or polyphosphoric acid. For example, phosphoric acid can be applied to an $SiO_2$, $Al_2O_3$ or pumice carrier by impregnation or spraying. This is followed, as a rule, by drying or calcination.

The oxidic catalysts can alternatively be used in the form of extrudates (e.g. 2–4 mm length), tablets (e.g. 3–5 mm diameter) or chips. Instead of the fixed-bed procedure, the catalysts can also be used as fluidized catalysts.

The reaction over the catalyst is carried out in the gas phase, as a rule at from 200° to 350° C., in particular from 230° to 300° C.

The reaction takes place in 2 steps, the smooth formation of a carbamic acid and its catalytic cyclization in accordance with the following equations:

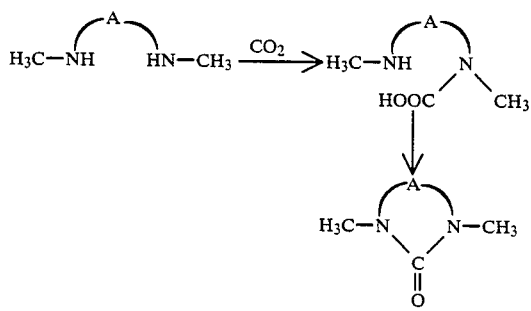

The starting materials used are diamines II in which the radicals on the nitrogen are each alkyl of 1 to 8, in particular 1 to 4, carbon atoms, e.g. methyl, ethyl, propyl, butyl, pentyl, hexyl, heptyl or octyl. The ethylene bridges or propylene bridges may be unsubstituted or may carry from 1 to 6 alkyl radicals, each of 1 to 17 carbon atoms. Advantageously, $R^3$ to $R^8$ are each alkyl of 1 to 12, in particular 1 to 8, carbon atoms in the abovementioned radicals. Because they are more readily obtainable, and in view of their use as polar solvents, starting materials having low molecular weight alkyl radicals $R^1$ to $R^8$ are preferably used.

The reaction of the diamine II with $CO_2$ can be carried out batchwise or, advantageously, continuously under reduced, slightly superatmospheric or, in particular, atmospheric pressure. For example, the diamine can be vaporized continuously, brought to the desired temperature and mixed with the $CO_2$ stream, which may have been preheated. It is also possible additionally to use an inert carrier gas, for example nitrogen or argon, or to employ sparingly volatile starting materials in the presence of an entraining agent.

The reaction mixture may have a molar ratio of 1:1 or may contain excess $CO_2$ or excess diamine. In general, a $CO_2$ excess of from 5 to 100 mol %, based on the diamine, is preferred, in order completely to convert the diamine and to absorb the heat liberated.

The reaction mixture can advantageously be passed over the catalyst at a rate such that about 0.5–5, preferably about 1–3, moles of diamine are converted per liter of catalyst per hour.

Working up of the resulting reaction mixture and isolation of the products can be carried out in a conventional manner, so that no further descriptions are required here. For example, the reaction mixture can be cooled and the desired product condensed together with the water of reaction or the product and the water of reaction condensed in succession. The product can be freed from water and purified, these steps being carried out by distillation. If required, unconverted diamine or diamine which has been converted only as far as the carbamic acid, can readily be recovered.

Among the substances which can be prepared according to the invention, in particular 1,3-dimethyl-2-imidazolidinone has so far been used industrially as a solvent or reaction medium. However, this product has the disadvantage that its melting point is about 8° C. Hence, it cannot be used or handled at lower temperatures. We have found that the previously unknown compound 1,3,4-trimethyl-2-imidazolidinone solidifies at an unexpectedly low temperature, i.e. as low as -34° C., and thus avoids the stated disadvantages.

EXAMPLE 1

For the preparation of 1,3-dimethyl-2-imidazolidinone, the reactor used was a vertical, heated glass tube whose upper part (length 50 cm) served as an evaporator and preheater and whose lower part (length 1 cm, volume 1,300 ml) served as a fixed-bed reactor. The upper part was filled with glass rings and contained a $CO_2$ inlet tube which extended as far as the beginning of the catalyst zone. The catalyst used was $\gamma$-$Al_2O_3$ in the form of extrudates. 1.5 moles/hour of N,N'-dimethylethylenediamine were pumped in at the upper end of the glass ring packing. At the same time, 2 moles/hour of $CO_2$ were fed through the inlet tube. The glass tube was heated at 250–280° C. After cooling to room temperature, the reaction mixture formed passed from the lower end of the reactor into a liquid separator. The collected liquid was distilled. Initially, a water fraction was obtained under atmospheric pressure, after which 1,3-dimethyl-2-imidazolidinone (boiling point 123–125° C./50 mbar, melting point +8° C.) was obtained in pure form under reduced pressure. Small amounts of the product could still be obtained from the water fraction by distillation.

The total yield was 99% of theory.

EXAMPLE 2

For the preparation of 1,3,4-trimethyl-2-imidazolidinone, the apparatus described in Example 1 was used under the same conditions, but 1,Z-bismethylaminopropane was reacted with $CO_2$. The yield of 1,3,4-trimethyl-2-imidazolidinone was 99% of theory. The compound has a boiling point of 225–227° C., a melting point of −34° C. and a density of 1.032 g/ml at 23° C.

EXAMPLE 3

The reaction described in Example 1 was repeated under the same conditions, except that an aluminum silicate containing 52% of $SiO_2$ and 48% of $Al_2O_3$ was used as the catalyst. The conversion of the N,N'-dimethylethylenediamine was about 80%, the remainder being recovered. The selectivity of the 1,3-dimethyl-2-imiazolidinone was 90%. A similar result was obtained using a silica catalyst.

EXAMPLE 4

1,3-bismethylaminopropane was reacted with $CO_2$ similarly to Example 1. The yield of 1,3-dimethyltetrahydropyrimidin-2-one was 99% of theory. The compound has a boiling point of 229–231° C.

When a 1,3-bismethylaminopropane having a purity of only 80% was used, the resulting yield was likewise 99%, the stated purity being taken into account in the calculation.

We claim:

1. A process for the preparation of an N,N'-dialkyl-substituted cyclic urea derivative of the formula I

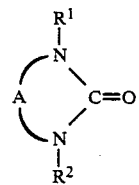

where $R^1$ and $R^2$ are each alkyl of 1 to 8 carbon atoms and A is $CR^3R^4$-$CR^5R^6$- or $CR^3R^4$-$CR^5R^6$-$CR^7R^8$, where $R^3$ to $R^8$ are each hydrogen or alkyl of 1 to 17 carbon atoms, by reacting a diamine of the formula II

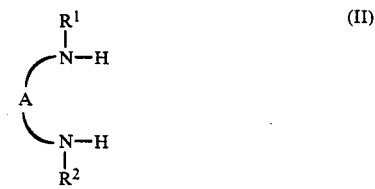

with carbon dioxide, wherein the reaction is carried out in the gas phase in the presence of an oxide of an element of main group three or four or subgroup two to six of the Periodic Table, or a mixture of these, or in the presence of an aluminum silicate or magnesium silicate.

2. A process as claimed in claim 1, wherein the catalyst used is $\gamma$-$Al_2O_3$.

3. A process as claimed in claim 1, wherein the catalyst used is a zeolite.

4. A process as claimed in claim 1, wherein the catalyst contains acidic constituents.

5. A process as claimed in claim 1, wherein $R^1$ and $R^2$ are each alkyl of 1 to 4 carbon atoms and A is $CR^3$-$R^4$-$CR^5R^6$ or $CR^3R^4$-$CR^5R^6$-$CR^7R^8$, where $R^3$ to $R^8$ are each hydrogen or alkyl of 1 to 4 carbon atoms.

6. A process as claimed in claim 1, wherein the reaction is carried out at from 200° to 350° C.

7. A process as claimed in claim 1, wherein the reaction is carried out by a continuous procedure.

* * * * *